United States Patent [19]

Chignac et al.

[11] E Re. 31,260

[45] Reissued * May 31, 1983

[54] PROCESS FOR THE PREPARATION OF AN ACETONITRILE DERIVATIVE

[75] Inventors: Michel Chignac, Sisteron; Claude Grain, Volonne; Charles Pigerol, Saint-Ouen, all of France

[73] Assignee: Labaz, Paris, France

[ * ] Notice: The portion of the term of this patent subsequent to Nov. 28, 1995, has been disclaimed.

[21] Appl. No.: 163,702

[22] Filed: Jun. 27, 1980

Related U.S. Patent Documents

Reissue of:

[64] Patent No.: 4,155,929
Issued: May 22, 1979
Appl. No.: 904,461
Filed: May 10, 1978

U.S. Applications:

[63] Continuation of Ser. No. 800,346, May 25, 1977, abandoned.

[30] Foreign Application Priority Data

Mar. 15, 1977 [FR] France ..... 77 07587

[51] Int. Cl.[3] ..... C07C 120/00; C07C 121/16

[52] U.S. Cl. ..... 260/465.1

[58] Field of Search ..... 260/465.1

[56] References Cited

PUBLICATIONS

Marshal, *J. Chem. Soc.*, (1930), pp. 2754–2761.
Brown et al., *J.A.C.S.*, (1955), 77, pp. 1083–1089.
Newman et al., *J.A.C.S.*, (1960), 82, pp. 873–875.
Hessler et al., *J.A.C.S.*, (1921), 43, pp. 205–208.
Newman et al., *J.A.C.S.*, (1958), 80, pp. 6350–6355.

*Primary Examiner*—Joseph Paul Brust
*Attorney, Agent, or Firm*—Mason, Kolehmainen, Rathburn & Wyss

[57] ABSTRACT

Process for the preparation of di-n-propyl acetonitrile of the formula:

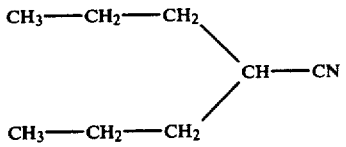

whereby, in a single step, sodium n-propylate in n-propanol medium is added to a reaction medium which is formed of a cyanacetate of general formula:

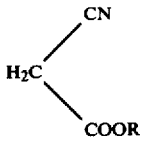

in which R represents an alkyl radical having from 1 to 4 carbon atoms, and n-propyl bromide or iodide, the alkylation reaction taking place under reflux, the crude ester obtained is saponified with a 10 to 20% solution of sodium hydroxide or potassium hydroxide, the resulting salt is acidified with a strong acid, to give crude di-n-propyl cyanacetic acid, which is decarboxylated by heating at a temperature between 140° C. and 190° C., so as to obtain the di-n-propyl acetonitrile.

9 Claims, No Drawings

PROCESS FOR THE PREPARATION OF AN ACETONITRILE DERIVATIVE

Matter enclosed in heavy brackets [ ] appears in the original patent but forms no part of this reissue specification; matter printed in italics indicates the additions made by reissue.

This application is a continuation of Ser. No. 800,346 filed May 25, 1977, now abandoned.

The present invention relates generally to a novel process for the preparation of an acetonitrile derivative and also to the derivative obtained by this process.

The invention is particularly concerned with a novel process for the preparation of di-n-propyl acetonitrile of formula:

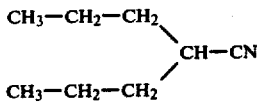

I

Di-n-propyl acetonitrile is a known product which is of particular interest for the preparation of compounds having pharmacological properties. For example, di-n-propyl acetonitrile can be used for the preparation of di-n-propyl acetamide, which has extremely valuable neuropsychotropic properties, as described in B.S.M. (French Special Medicament Patent) No. 2442 M.

Di-n-propyl acetamide can be easily prepared with excellent yields, of the order of 83%, when starting from the di-n-propyl acetonitrile, by hydrolysing this latter compound, for example, by means of an aqueous solution of 75to 80% sulphuric acid and at a temperature between 80° and 130° C.

The conventional processes for the preparation of di-n-propyl acetonitrile are generally complicated and necessitate the use of reactants which are dangerous for the manufacturing personnel. For example, the preparation of di-n-propyl acetonitrile, when starting from di-n-propyl ketone, requires the use of sodium cyanide, which is an extremely toxic product.

Moreover, certain phases in the preparation consist in a hydrogenation, which is always difficult to carry out on the industrial plane.

The need for finding an industrial process for obtaining di-n-propyl acetonitrile is thus of paramount importance.

Hitherto, the synthesis of acetonitrile substituted in the $\alpha$-position by two propyl groups, starting from an ester of cyanacetic acid, has only been subject to experimentation in the case where each of the two propyl groups is an isopropyl group.

In this connection, mention may be made of the processes described by MARSHALL [J. Chem. Soc., 2754–2761 (1930)], by BROWN and collaborators [J. Am. Chem. Soc., 77, 1083–1089 (1955)] and by NEWMAN and collaborators [J. Am. Chem. Soc., 82, 873–875 (1960)].

These processes are characterised by a succession of three or four quite distinct stages or steps, starting from an ester of cyanacetic acid, namely:

an alkylation phase, which is common to all three processes, for the purpose of obtaining a diisopropyl cyanacetic ester, a phase for elimination of the monoalkylated ester, a phase for saponification of the diisopropyl cyanacetic ester in the case of the processes proposed by MARSHALL and NEWMAN and collaborators, and a decarboxylation phase, either of the diisopropyl cyanacetic ester in the case of the process proposed by BROWN and collaborators, or of the diisopropyl cyanacetic acid in the case of the processes proposed by MARSHALL and by NEWMAN and collaborators.

Thus, MARSHALL prepares diisopropyl acetonitrile from a cyanacetic ester, by treating with sodium an alcoholic solution of this ester and by causing this mixture to react for several hours with an excess of isopropyl iodide. The monoalkylated product is eliminated by means of a 10% sodium hydroxide solution and the crude dialkyl ester obtained by this procedure is then treated with a 35% potassium hydroxide solution for 16 hours. After acidification, the diisopropyl cyanacetic acid obtained is decarboxylated by distillation in the presence of twice its weight of molten potassium hydroxide.

BROWN and collaborators, for their part, obtain diisopropyl acetonitrile first of all by treating, with isopropyl iodide, a solution of cyanacetic ester in n-propanol containing sodium n-propylate, this being effected by refluxing for 2 hours, and then by again adding sodium n-propylate in n-propanol and isopropyl iodide. The reaction medium is once again heated under reflux for 3 hours, the monoalkylated product is eliminated by a 10% sodium hydroxide solution and the diisopropyl cyanacetic ester is then distilled several times in the presence of twice its weight of potassium hydroxide.

Finally, NEWMAN and collaborators prepare diisopropyl acetonitrile by first of all carrying out a reaction, under reflux for 3 hours, of ethyl cyanacetate with isopropyl iodide in the presence of sodium ethylate in ethanolic medium, further adding sodium ethylate and then isopropyl iodide and once again heating the reaction medium under reflux for 3 hours. After again adding sodium ethylate and then isopropyl iodide and heating for 2 hours under reflux, the disopropylated derivative obtained is washed with a 15% potassium hydroxide solution and then hydrolysed by means of an alcoholic solution of 35% potassium hydroxide under reflux for 26 hours and the diisopropyl cyanacetic acid is heated to 180°–200° C. in the presence of copper powder.

In view of the great similarity as regards chemical structure between diisopropyl acetonitrile and di-n-propyl acetonitrile, attempts have been made to prepare this latter compound by applying the aforementioned processes used for the preparation of the diisopropyl acetonitrile.

Tests carried out with the technique proposed by MARSHALL only produced insignificant yields of pure di-n-propyl acetonitrile, of the order of 20%, if each synthesis intermediary is purified, or 35%, if each intermediary is used in the crude state, these yields being calculated on the basis of the initial cyanacetic ester. Furthermore, the intermediate products prepared in this process are contaminated with impurities, which prevent their use in the crude state. Thus, the crude di-n-propyl cyanacetic acid obtained according to MARSHALL, or according to NEWMAN and collaborators, is found to be contaminated by 18 to 25%, and 32 to 34%, respectively, of a product which seems to be a di-n-propyl formamidoacetic ester.

Furthermore, the procedure proposed by BROWN and collaborators, as it necessitates a double alkylation phase, has proved to be inadequate for the preparation of di-n-propyl acetonitrile. In effect, this product has been obtained in pure form with yields which vary from 28 to 44%, calculated from the initial methyl cyanacetate.

Finally, the process proposed by NEWMAN and collaborators, which necessitates a treble alkylation phase and is particularly time-consuming, only provided yields in the region of 40% of pure di-n-propyl acetonitrile, calculated on the basis of the initial cyanacetic ester. It has also been observed that the saponification of the di-n-propyl cyanacetic ester leads to a mixture of 10% of di-n-propyl acetic acid and 5% of di-n-propyl acetic amide.

In conclusion, all of the aforesaid methods, applied to the preparation of di-n-propyl acetonitrile, are essentially distinguished by their complexity and their considerable duration, by the impurities obtained at the different stages, necessitating the elimination of such impurities for the subsequent stages, and by the poor yields of the final di-n-propyl acetonitrile.

Consequently, it was essential to find a process for the preparation of di-n-propyl acetonitrile which has the following qualities:

simplicity as regards procedure,
shorter overall duration,
higher yields,
a production cost which is as low as possible, so that it can be validly used on the industrial scale.

In accordance with the present invention, it has now been discovered that di-n-propyl acetonitrile can be obtained in accordance with such a process which can be used industrially, starting from a cyanacetic ester.

Thus in accordance with the process of the invention, di-n-propyl acetonitrile is prepared by reacting, in one single stage and in a n-propanol medium, an ester of cyanacetic acid of the general formula:

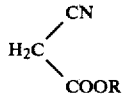

II in which R represents an alkyl radical having from 1 to 4 carbon atoms, preferably a methyl or ethyl radical, with n-propyl bromide or n-propyl iodide in the presence of sodium n-propylate, then by saponifying the crude ester thus obtained with a 10 to 20% by weight solution of potassium hydroxide or sodium hydroxide and by acidifying the salt thus formed with a strong acid, such as for example hydrochloric acid, to obtain the crude di-n-propyl cyanacetic acid, which is decarboxylated by heating to a temperature between 140° C. and 190° C., this yielding the di-n-propyl acetonitrile.

The starting-products of formula II are either known products which have been mentioned in the foregoing publications, or products which can be obtained by known methods.

As regards the alkylation phase, the reactants are utilised by adding, at a temperature between 45° C. and 55° C., the sodium n-propylate in n-propanol medium to a reaction medium which comprises the cyanacetic ester and the n-propyl halide. The alkylation reaction is then carried out under reflux for about 3 hours.

Saponification of the crude di-n-propyl cyanacetic ester is preferably carried out at a temperature between 60° and 70° C. over a period of 3 hours in the proportion of 1.25 to 2 mols of hydroxide/mol of ester, and the subsequent acidification is effected, for example, with a 36% hydrochloric acid solution, at a temperature slightly lower than 40° C.

In accordance with an alternative procedure, the saponification phase can be carried out in presence of a quaternary ammonium salt such as, for example, trimethyl cetylammonium bromide, benzyl trimethyl ammonium chloride or lauryl trimethyl ammonium bromide. The concentration of quaternary ammonium salt may vary from 0.005 mol to 0.1 mol/mol of di-n-propyl cyanacetic ester. Temperature as regards saponification and the time necessary for this operation will vary as a function of the quantity of quaternary ammonium salt used.

For a concentration of quaternary ammonium salt of 0.1 mol/mol of ester, saponification will take place for 3 hours at 30° C., and for a concentration of 0.005 mol/mol of ester, the operation will be completed in 1 hour at 60° to 65° C.

As regards the decarboxylation phase, this latter will be carried out on the crude di-n-propyl cyanacetic acid at a temperature between 140° and 190° C. and preferably between 175° and 190° C.

In accordance with a modification of this last operation, the decarboxylation of the di-n-propyl cyanacetic acid can be carried out in one continuous phase. After the acid concerned is brought to a temperature of 185°-190° C. and the decarboxylation reaction initiated, di-n-propyl cyanacetic acid is continuously introduced, with simultaneous elimination of the liberated carbon dioxide gas and of the di-n-propyl acetonitrile which forms.

The process of the invention provides indisputable advantages as compared with the processes disclosed in the previously mentioned prior art.

In the first place, the process of the invention offers the possibility of obtaining considerable yields of pure di-n-propyl acetonitrile, the yields being at least 80% as compared with the initial cyanacetic ester, whereas with the processes suggested by the prior art, it has not been possible to obtain yields higher than 50% with respect to the same starting ester.

In addition, the process of the invention is definitely more simple than those of MARSHALL, BROWN and collaborators, or NEWMAN and collaborators, referred to above. For example, the process of the invention permits the alkylation phase to be carried out in one single operation, comprising a single use of the n-propyl halide and alkali metal n-propylate.

By contrast, the process proposed by BROWN and collaborators necessitates two successive additions of alcoholate and of halide, while in accordance with the process proposed by NEWMAN and collaborators the addition of alcoholate and of halide is carried out in three successive operations for each product.

The times necessary for the alkylation and saponification phases are also considerable in the case of the known processes: at least 8 hours for the alkylation phase according to the process proposed by NEWMAN and collaborators, and 26 hours for the saponification phase, according to these same authors.

The process of the invention, on the contrary, enables the corresponding alkylation and saponification phases to be effected much more quickly than by means of the known processes.

As regards the saponification phase, the time which is necessary for this operation will be advantageously reduced in the presence of a quaternary ammonium salt, for example, the trimethyl cetylammonium bromide. This quaternary ammonium salt offers in addition the advantage of reducing the danger of hydrolysis of the nitrile function of the di-n-propyl cyanacetic ester.

Furthermore, the decarboxylation phase of the known processes involves the necessity, apart from a raising of the temperature, of adding a supplementary product, either potassium hydroxide or copper powder.

According to the invention, the decarboxylation phase occurs simply by heating the di-n-propyl cyanacetic acid.

An additional disadvantage presented by the processes suggested by the prior art, and more especially by the alkylation phases envisaged in these processes, is concerned with the recovery of the solvent, of the reactants which have not reacted and of the by-products formed during the reaction.

This recovery, which is fairly difficult when using sodium ethylate/ethanol or sodium methylate/methanol is facilitated by the use of the sodium n-propylate/n-propanol pair, which provides greater possibility of separation by distillation of the unreacted n-propyl halide, of the ether formed during the reaction and of the alcohol which may be liberated by transesterification of the cyanacetic ester by the n-propanol.

All these disadvantages, presented by the processes suggested by the prior art, increase the quantity of material to be used, the labour force and the energy consumption, causing a concurrent increase in the cost of production.

Among the disadvantages presented by the known processes, the presence of harmful impurities at the different stages is certainly not the least negligible.

These impurities, which are present at each phase of the process, singularly complicate the successful performance of the said process. Consequently, it is necessary for them to be eliminated at each stage, thus considerably increasing the intermediate handling operations, which are always costly at the industrial level.

For example, the processes suggested by the prior art envisage the elimination of the monoalkylated product after the alkylation phase, this being effected by means of 10% potassium hydroxide.

The alkylation phase as envisaged within the scope of the process according to the invention renders unnecessary the intermediate purification of the di-n-propyl cyanacetic ester, which may be used in its crude form.

It has, in fact, been observed that the use of the alkylation reactants according to the invention, depending essentially on the introduction of sodium n-propylate/n-propanol into a medium formed by the ester of formula II and the n-propyl halide, provides the particular advantage of avoiding to a maximum extent the formation of monopropyl cyanacetic ester, which is much greater when the n-propyl halide is added to the cyanacetic ester/sodium-n-propylate mixture. This monopropyl cyanacetic ester, does, in fact, eventually lead to the formation of valeronitrile, which is a particular nuisance and must be eliminated.

The use of the alkylation reactants in accordance with the invention permits the content of valeronitrile in the final di-n-propyl acetonitrile to be very substantially reduced, this content passing from approximately 3.6% to only 0.3% according to the invention.

Furthermore, the use of sodium n-propylate/n-propanol in accordance with the invention has been found to be much more advantageous than the use of sodium ethylate/ethanol or the use of sodium methylate/methanol, as proposed in the processes according to the prior art.

It has, in fact, been established that the content of monopropyl cyanacetic ester in the crude di-n-propyl cyanacetic ester, which subsequently leads to valeronitrile, is increased, and can even vary from 2 to 5% if the reflux temperature of the reaction medium is too low at the time of the alkylation phase, which is the case with methanol or ethanol.

It has also been found that the use of the sodium ethylate/ethanol pair can give rise to the formation of a not inconsiderable quantity, in the region of 1%, of n-propyl cyanacetic ethylate at the time of the alkylation phase.

Moreover, as previously mentioned, the saponification of the crude di-n-propyl cyanacetate in accordance with the conditions proposed by NEWMAN and collaborators, or by MARSHALL, that is to say, by means of 35% potassium hydroxide for 16 to 26 hours, leads to the formation of a crude di-n-propyl cyanacetic acid containing from 18 to 34% of an impurity, which seems to be a di-n-propyl formamidoacetate and has to be eliminated. This last product does not, in fact, give di-n-propyl acetonitrile by decarboxylation, but di-n-propyl acetamide.

Yet again, the process according to the invention avoids this disadvantage and, at the same time, an intermediate purification of the crude di-n-propyl cyanacetic acid.

During tests carried out within the scope of the present invention, attempts have been made to combine certain phases characteristic of the process of the invention with phases which are used by the previously mentioned prior processes.

For example, the dialkylation phase of the process according to the invention, combined with the decarboxylation stage of the di-n-propyl cyanacetic acid by being melted with twice its weight of 85% potassium hydroxide, at a temperature between 190° and 360° C., in accordance with the procedure proposed by MARSHALL, only supplied 11% of di-n-propyl acetonitrile with respect to the cyanacetic ester used. In this method of procedure, most of the di-n-propyl cyanacetic acid was transformed into di-n-propyl acetamide and di-n-propyl acetic acid.

A variation of the decarboxylation process proposed by MARSHALL has also been carried out with di-n-propyl cyanacetic acid, obtained according to the process of the invention, and twice its weight of 98% sodium hydroxide. This mixture, distilled for 2¼ hours at 370° C., only supplied 38.3% of di-n-propyl acetonitrile with respect to the di-n-propyl cyanacetic acid used.

Furthermore, the methyl di-n-propyl cyanacetate obtained in accordance with the process of the invention, was distilled in the presence of potassium hydroxide, following the procedure of BROWN and collaborators.

By using twice as much by weight of 97.7% potassium hydroxide as of ester and by heating to 380° C. for at least 2¼ hours, only 28.4% of pure di-n-propyl acetonitrile, relatively to the initial cyanacetate, were obtained.

A similar test, carried out with the same quantity of 98% sodium hydroxide, under the same conditions as regards temperature and duration, provided a yield of 44.4% of di-n-propyl acetonitrile relatively to the initial cyanacetate.

From all the results set out above, it is obvious that the process according to the invention constitutes an undoubted advantage over the processes suggested by the prior art.

Furthermore, the process of the invention has proved to be superior to the known process as used for preparing di-n-propyl acetonitrile, which process has been previously referred to.

The invention is illustrated by the following non-limiting Examples:

EXAMPLE 1

Preparation of di-n-propyl acetonitrile

(a) Di-n-propyl cyanacetic acid

First of all, a sodium n-propylate solution was prepared from 7.42 g (0.322 mol) of sodium and 180 ml of anhydrous n-propanol, by heating with gentle reflux until complete dissolution of the sodium.

Into a 500 ml spherical flask, equipped with a dropping funnel, a mechanical stirrer, a thermometer and a condenser, above which was disposed a calcium chloride trap, were introduced 16.95 L g (0.141 mol) of ethyl cyanacetate and 40.69 g (0.33 mol) of n-propyl bromide. This mixture was heated to 45° C. and then there was added thereto, slowly and while stirring, the previously prepared solution of sodium n-propylate, keeping the temperature of the reaction medium at 50°-55° C. by gentle external cooling.

With the completion of the operation of introduction, the mixture was brought to reflux temperature in 30 minutes and kept at this temperature for 3 hours. The n-propanol was then distilled and the distillation stopped when the temperature of the residual mass had reached 115° C.

The crude ester obtained in this way was then treated with a solution of 7.5 g of flaked sodium hyroxide in 67.5 ml of water. The mixture was introduced into a 250 ml spherical flask, equipped with a condenser, and then the reaction medium was slowly brought to 60°-70° C. This temperature was maintained for 3 hours, whereafter the mixture was cooled to about 50° C. and the ethanol which had formed and the residue of n-propanol were eliminated under a pressure of 70 mm.Hg. The solution thus obtained was cooled to 20° C. and acidified, while stirring, by addition of 26.25 g of 36% hydrochloric acid. During this operation, the temperature of the reaction medium was kept below 40° C. by cooling. Stirring was continued for 30 minutes, whereafter the mixture was left standing for 30 minutes. The oily layer of di-n-propyl cyanacetic acid was decanted and the aqueous phase extracted with 35 ml of toluene. The extract in toluene was then added to the decanted di-n-propyl cyanacetic acid, whereafter the solution in toluene was washed, in a separation funnel, with a solution of 1.5 g of sodium chloride in 14 ml of water. The toluenic phase was decanted and the toluene distilled under atmospheric pressure.

Using this procedure, 25 g of crude di-n-propyl cyanacetic acid were obtained.

(b) Di-n-propyl acetonitrile

Into a 100 ml spherical flask fitted with a thermometer and a condenser were introduced 25 g of crude di-n-propyl cyanacetic acid obtained by the method previously described, and the mixture was heated on an oil bath.

Decarboxylation commenced at a temperature in the region of 140° C. The mixture was then brought to reflux temperature, that is to say, to about 160° C. and then to 190° C. in 2 hours. This temperature was maintained until the release of gas was completed, this taking 2 hours. The di-n-propyl acetonitrile thus formed was then slowly distilled and the fraction passing over between 165° C. and 175° C. was collected. A second distillation was then carried out.

Using this procedure, 14.7 g of di-n-propyl acetonitrile were collected. B.P.:170° C.

Yield: 83%, relatively to the ethyl cyanacetate used.

EXAMPLE 2

Preparation of the di-n-propyl acetonitrile

(a) Di-n-propyl cyanacetic acid

Initially, a solution of sodium n-propylate was prepared from 50 g (2 at.g +10%) of sodium and 804 g (1000 ml) of anhydrous n-propanol, by heating to 50°-55° C. for 60 to 90 minutes.

99.1 g (1 mol) of methyl cyanacetate and 270.6 g (2.2 mols) of n-propyl bromide were introduced into a 2-liter spherical flask. While stirring, the mass was brought to 45°-50° C. and, at this temperature, the solution of sodium n-propylate in propanol was regularly introduced. This operation lasted from 60 to 75 minutes.

When the operation of introduction was completed, the mixture was refluxed for 3 hours. The n-propanol was then distilled until a temperature of 120°-125° C. was reached in the residual mass. The crude ester obtained was then treated with 500 g of a 10% aqueous solution of sodium hydroxide and with 0.36 g of cetyl trimethyl ammonium bromide.

The mixture was brought to reflux for 1 hour, was then cooled to about 50° C., and thereafter the residual alcohols were eliminated under reduced pressure (50 to 100 mm.Hg).

The solution obtained was cooled and then acidified, without exceeding 40° C., by means of 175 g of 36% hydrochloric acid. The mixture was maintained in this state for 30 minutes and then the di-n-propyl cyanacetic acid was decanted. The lower aqueous layer was extracted with 250 g of toluene. The two organic phases were combined, washed once with 100 g of purified water and the solvent eliminated by distillation under reduced pressure, to obtain 154.5 g of crude di-n-propyl cyanacetic acid.

(b) Di-n-propyl acetonitrile

The previously obtained crude di-n-propyl cyanacetic acid was transferred into a 250 ml spherical flask and progressively brought to reflux, while eliminating the last traces of toluene by means of a Dean-Stark system, until a temperature of the mass in the region of 175° to 180° C. was obtained. Decarboxylation started in the region of 140° C. and the reaction was practically complete after 1 hour of reflux. The mixture was kept for a total of 2 hours under reflux. The mass temperature reached 205°-210° C. in the first few minutes of the refluxing operation, and dropped down again and became stable in the region of 185° C. The mixture was then distilled at atmospheric pressure.

In this manner, 102.5 g of di-n-propyl acetonitrile were recovered. Yield of crude product: 82%, relatively to the methyl cyanacetate.

Yield of pure product: 80%.

EXAMPLE 3

Preparation of di-n-propyl acetonitrile

Into a 50-liter enamelled container were introduced 30 kg of di-n-propyl cyanacetic acid. While stirring, heating under reflux to 185°–190° C. was carried out and the temperature was maintained as such for 15 minutes. The di-n-propyl acetonitrile thus formed was distilled, while 69.4 kg of di-n-propyl cyanacetic acid were continuously introduced.

The speed of introduction was regulated as a function of the speed of distillation of the nitrile, while the temperature of the mass was maintained at 185°–190° C. The operation of introduction lasted for about 4½ hours, during which 40.9 kg of crude di-n-propyl acetonitrile were recovered. Distillation was continued by gradually raising the temperature of the mass to 206° C. and until the operation was completed. This operation lasted 6 hours, during which there were recovered 16.350 kg and then a further 8.980 kg of crude di-n-propyl acetonitrile.

The apparatus was brought under reduced pressure (about 100 mm.Hg) and a new fraction of 1.640 kg of di-n-propyl acetonitrile was collected.

Using this procedure, 67.87 kg of crude di-n-propyl acetonitrile were obtained.

We claim:

1. Process for the preparation of di-n-propylacetonitrile of the formula:

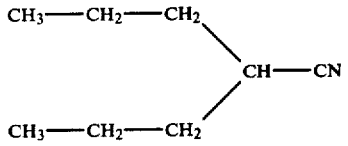

whereby, (a) sodium n-propylate in n-propanol medium is added to a reaction medium which is formed of a cyanacetate of general formula:

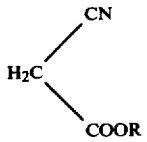

in which R represents an alkyl radical having from 1 to 4 carbon atoms, and n-propyl bromide or iodide, the alkylation reaction taking place under reflux at atmospheric pressure, (b) the crude ester obtained is saponified at a temperature between 30° and 70° C. with a 10 to 20% by weight solution of sodium hydroxide or potassium hydroxide in the proportion of 1.25 to 2 mols of sodium or potassium hydroxide per mol of crude ester, the resulting salt is acidified with a strong acid at a temperature not exceeding 40° C., to give crude di-n-propyl cyanacetic acid, (c) which is decarboxylated solely by heating, in the absence of any supplementary agent, at a temperature between 140° C. and 190° C., so as to obtain the di-n-propylacetonitrile.

2. Process according to claim 1, wherein the cyanacetate is methyl cyanacetate or ethyl cyanacetate.

3. Process according to claim 1, whereby the addition of sodium n-propylate is carried out when the temperature of the reaction medium is at 45° C. to 55° C.

4. Process according to claim 1, whereby the saponification is effected in the presence of a quaternary ammonium salt.

5. Process according to claim 4, wherein the quaternary ammonium salt is trimethyl cetylammonium bromide.

6. Process according to claim 4, whereby the saponification is carried out in the presence of 0.005 to 0.1 mol of quaternary ammonium salt mol of crude ester.

7. Process according to claim 1, whereby the acidification takes place by means of 36% hydrochloric acid at a temperature which does not exceed 40° C.

8. Process according to claim 1, whereby the decarboxylation takes place at a temperature which is between 175° and 190° C.

9. Process according to claim 1, whereby the decarboxylation operation is carried out by continuously transferring the di-n-propyl cyanacetic acid into the decarboxylation medium and by simultaneously eliminating the formed di-n-propyl acetonitrile.

* * * * *